United States Patent [19]

Ochi et al.

[11] Patent Number: 5,196,337

[45] Date of Patent: Mar. 23, 1993

[54] HUMAN MONOCLONAL ANTIBODY, AND ITS PRODUCTION AND USE

[75] Inventors: Hiroshi Ochi, Osaka; Hiroshi Ohtsuka, Hyogo; Shinichi Yokota, Hyogo; Hiroshi Noguchi, Kawanishi; Masazumi Terashima, Ibaraki; Ikuko Uezumi, Osaka; Kenji Irie, Kawanishi, all of Japan

[73] Assignees: Sumitomo Chemical Company, Limited; Sumitomo Pharmaceuticals Company, Limited, both of Osaka, Japan

[21] Appl. No.: 513,933

[22] Filed: Apr. 24, 1990

[30] Foreign Application Priority Data

Apr. 24, 1989 [JP] Japan ................... 1-104849

[51] Int. Cl.$^5$ .......................... C12N 5/12; C12P 21/08; C07K 15/28
[52] U.S. Cl. ................... 435/240.27; 435/70.21; 530/388.4; 530/388.15; 530/388.2
[58] Field of Search ............... 530/387, 388, 388.4, 530/388.15, 388.2; 935/100, 104, 110, 107, 108; 435/70.21, 7, 240.27

[56] References Cited

U.S. PATENT DOCUMENTS 4,918,163 4/1990 Young et al. .................. 530/387

FOREIGN PATENT DOCUMENTS 0163493 12/1985 European Pat. Off. .
0256713  3/1987 European Pat. Off. .
0326148  8/1989 European Pat. Off. .
0341684 11/1989 European Pat. Off. .
2185266  7/1987 United Kingdom .

OTHER PUBLICATIONS

Kozbor, D. et al., Eur. J. Immunol., 14:23-27 1984.
Teng, N. N. H. et al., Proc. Natl. Acad. Sci., 82:1790-1794, Mar. 1985.
Zeerink et al., Infection and Immunity, vol. 56, No. 8, pp. 1873-1879, 1988.

Primary Examiner—John J. Doll
Assistant Examiner—Susan L. Futrovsky
Attorney, Agent, or Firm—Birch, Stewart, Kolasch & Birch

[57] ABSTRACT

A human monoclonal antibody, which has prophylactic and therapeutic effect to infectious diseases caused by Pseudomonas aeruginosa of serotypes A and H classified under the Japanese Committee's Classification, and the epitope of which is located at the common structure in the O-antigen of Pseudomonas aeruginosa of serotypes A and H. A hybridoma producing said human monoclonal antibody, and processes for preparing said hybridoma and antibody are also provided.

3 Claims, 1 Drawing Sheet

HUMAN MONOCLONAL ANTIBODY, AND ITS PRODUCTION AND USE

BACKGROUND OF THE INVENTION

1. Field of the Invention

The present invention relates to a human monoclonal antibody to *Pseudomonas aeruginosa* (hereinafter referred to as "*P. aeruginosa*"), and its production and use. More particularly, it relates to a human monoclonal antibody, which can recognize a partial structure of O-antigen common to A and H serotype strains of *P. aeruginosa*, and which shows a binding property to *P. aeruginosa* of various strains of different serotypes, and its use. It also relates to a hybridoma capable of producing the antibody, and a process for the production of the antibody. The human monoclonal antibody of the invention is useful for prevention and treatment of infectious diseases caused by *P. aeruginosa*. It is also useful for diagnosis of infectious diseases caused by *P. aeruginosa*.

2. Description of Related Art

Bacteria causing infectious diseases, i.e. prophlogistic bacteria, are varied with development and change of antibiotics as clinically used. As a result, infectious diseases with bacteria originally having only low pathogenicity or virulence may increase. Thus, *P. aeruginosa* is currently one of the major pathogenic bacteria causing infectious diseases, of which serious symptoms often lead patients to death, particularly when their immunological competence is low due to continuous administration of immunosupressants, suffering from cancer or burn or the like.

Among various preventive or therapeutic methods for bacterial infections, the most prevailing one is chemotherapy by the use of antibiotics or antimicrobial agents. In fact, there have been developed various antibiotics including streptomycin, kanamycin, penicillin, cephalosporin, etc., which are sensitive to almost all Gram-positive bacteria (e.g. Staphylococci) and Gram-negative bacteria (e.g. *E. coli*) and produce a prominent clinical effect. However, there are known only few medicinal products active against to *P. aeruginosa*. Even those medicianl products act on *P. aeruginosa* only bacteriostatically and not bacteriocidally. Thus, they do not clinically exhibit any remarkable therapeutic effect.

The other preventive or therapeutic method is antibody therapy comprising administration of immunoglobulin. This method is often performed in association with chemotherapy and nowdays attracts much attention as a substitute for chemotherapy. A serum of high antibody titer can be obtained by active immunization of animals such as horse or rabbit, and antibody therapy can be made by administration of such serum. In fact, its remarkable therapeutic effect was proved on experimental infections using various animals. It is known from the cases of diphtheria toxin and viper toxin that antibody therapy using sera originated from animals is quite effective even on human beings. However, introduction of a heterogenous protein obtained from animals into a human body may cause such a serious side-effect as anaphylaxis or any other allergic reaction. It is thus highly desired to develop human immunoglobulin having a high antibody titer against bacteria and showing a prominent therapeutic effect on bacterial infections.

Conventional human immunoglobulin preparations are manufactured by collecting blood from healthy persons or bacteria-infected patients, subjecting the blood to fractionation to obtain an immunoglobulin fraction, purifying the immunoglobulin fraction and eliminating agglutinating materials therefrom by addition of ethylene glycol, treatment with protease, sulfonization, DEAE-column chromatography, etc., followed by formulation of the resulting product into intramuscularly or intravenously injectionable preparations. These preparations are advantageous in not causing anaphylaxis or any other side-effect as seen on administration of immunoglobulin originated from animals but they have some drawbacks. One such drawback is that their antibody titer against bacteria is low so that a sufficient therapeutic effect can not necessarily be produced. Another drawback is that their stable supply with a high antibody titer in a large amount is difficult, because they are manufactured using blood collected from healthy persons or bacteria-infected patients and the constant and continuous obtainment of sera having a high antibody titer is quite hard. A further drawback is that they may be contaminated with hepatitis virus (e.g. HB virus), Adult T cell leukaemia virus (ATLV, HTLV), etc., because the blood as the starting material is obtained from a number of unknown persons. In order to overcome these drawbacks, production of a human monoclonal antibody having a strongly protective effect on the infections with *P. aeruginosa* is highly desirable.

When an antibody is bound to the surface layer of a bacterial body, the phagocytosis of a macrophaze on the bacterial body is accelerated (i.e. acceleration of phagocytosis due to opsonization), or the lysis of the bacterial body by a complement takes place. As the target antigen at the surface layer of the bacterial body of *P. aeruginosa*, there are known lipopolysaccharide (LPS), outer membrane protein, flagellum, pilus, etc. Of these, Sawada et al. reported that a far large amount of a mouse monoclonal antibody recognizing the outer membrane protein is required in combatting bacteria as compared with a mouse monoclonal antibody which recognizes LPS (J. Infect. Dis., 150, 570–576 (1984)).

LPS consists of O-polysaccharide which represents O-antigen, an outer core oligosaccharide being common among species to some extent, an inner core oligosaccharide, of which component of saccharide, i.e. heptose or 2-keto-3-deoxyoctonate (KDO), is generally almost common to all enterobacteria, and lipid A. The O-polysaccharide antigen locating at the outermost surface of a bacterial cell consists of repeating units of 2 to 5 sugar residues, and its structure varies to a large extent. The structures of almost all O-antigens of the standard serotype strains of *P. aeruginosa* have already been determined (Eur. J. Biochem., 106, 643–651 (1980); ibid., 125, 229–237 (1986); ibid., 150, 541–550 (1985); ibid., 155, 659–669 (1986); ibid., 167, 549–561 (1987)).

Because determination of the structure of O-antigen by chemical analysis requires a lot of time and labor, antisera or mouse monoclonal antibodies against the O-antigens from the standard strains are employed for the classification of the strains of *P. aeruginosa*. Namely, an unknown strain of *P. aeruginosa* is classified in accordance with an immunological reactivity with known antibodies or antisera. This classification is known as a serotype, and typical examples of the serotype classification are as follows: Types 1 to 17 according to the classification by Homma et al. (Japan J. Exp. Med., 44, 1, (1974)); Types 1 to 7 according to the classification by Fisher et al (J. Bacteriol., 98, 835 (1969)); Types A to M according to the classification by Nippon Ryokunoh-kin Kenkyukai Kesseigatabetsu Kento Iinkai (Committee of Study on Serotype Classification, Japanese Study Group on Pseudomonas aeruginosa (hereinafter referred to as "Japanese Committee") (Japan J. Exp. Med., 45, 329 (1976)); Types 1 to 17 according to the classification by International Antigenic Typing System (IATS), etc. These classifications and their cross-relations are shown in Table 1 (Japan J. Exp. Med., 46, 329 (1976)).

TABLE 1

| Serotype classification of P. aeruginosa | | | |
|---|---|---|---|
| Japanese Commitee 1976 | Homma et al 1974 | IATS 1983 | Fisher et al 1969 |
| A | 1 | 3 | — |
| B | 2, 7, 13, 16 | 2, 5, 16 | 3, 7 |
| C | 3 | 8 | 6 |
| D | 4 | 9 | — |
| E | 5 | 11 | 2 |
| F | 6 | 4 | — |
| G | 8 | 6 | 1 |
| H | 9 | 10 | 5 |
| I | 10 | 1 | 4 |
| J | 11 | 15 | — |
| K | 12 | 13 | — |
| L | 14 | — | — |
| M | 15, 17 | — | — |
| — | — | 7, 12, 14, 17 | — |

It is known that the antibody specific to a certain O-antigen shows a strong preventive or therapeutic effect for P. aeruginosa infections of the serotype to which said O-antigen belongs but does not show any effect against P. aeruginosa in other serotypes. Consequently, for the production of prophylactic and therapeutic preparations by the use of the O-antigen specific monoclonal antibody, it is necessary to broaden its binding spectrum by mixing (hereinafter referred to as "cocktailing") plural monoclonal antibodies, respective antibodies being specific to respective O-antigens in different serotypes. However, the use of plural monoclonal antibodies necessitates the increase of production steps such as cultivation of antibody-producing cell lines, and purification of the monoclonal antibody therefrom makes the entire process very complicated, thereby raising problems in productivity and production cost, etc.

As stated above, the monoclonal antibody against outer membrane protein, like conventional antibodies against LPS core, is not sufficiently effective, although the binding spectra of the former is fairly broad in P. aeruginosa. Therefore, elimination of the problems as seen in production of the cocktail preparation comprising the anti O-antigen monoclonal antibodies is highly desirous. Namely, if one could produce a monoclonal antibody which specifically recognizes an O-antigen and exerts a significant prophylactic and therapeutic effective against infections caused by P. aeruginosa, while exerting a broad binding spectra to a large number of serotype strains, the cocktail preparation comprising said antibody may possibly require least numbers of other monoclonal antibodies. In other words, production of the cocktail preparation usable for a wide range of the serotype strains could be accomplished, even if it comprises least numbers of such monoclonal antibodies.

Fukuda et al. made a report on a specific human monoclonal antibody reactive with several O-antigens of P. aeruginosa (WO88/04669). However, this report only demonstrated that the monoclonal antibody binds to two types of LPS derived from different serotype standard strains of P. aeruginosa, and is still silent on whether said monoclonal antibody can specifically recognize the O-antigen in LPS. Further, on the basis of the reactivity shown with regard to one or two LPS derived from standard strains of P. aeruginosa, it is hardly difficult to conclude that such monoclonal antibody has a specific binding property to other strains within the same serotype. More specifically, Fukuda et al disclosed in their report eleven species of the monoclonal antibody (HPs 1, 2, 4, 5, 6, 7, 8, 9, 10, 11, 12), each being reactive to the LPS derived from standard strains of P. aerusinosa in Types D and I, E and F, A and L, G and H, E and F, and A and F, but no disclosure was made to the monoclonal antibody capable of specifically recognizing either LPS in Types A and H, particularly O-antigen therein.

Likewise, Zweerink et al. reported that they established a human monoclonal antibody which could bind to LPS of P. aeruginosa in serotypes B and C (corresponding to types 3, 6 and 7 according to Fisher's serotype classification) (Infect., Immun., 56, 1873–1879 (1988); JP-A-63-107999). Similar to the report by Fukuda et al., this report is suggestive of a certain antigen in LPS, which their monoclonal antiobdy specifically recognizes, but so far no specific disclosure was made on that antigen.

SUMMARY OF THE INVENTION

An extensive study has been made to establish a method for producing, in an industrial scale, a human monoclonal antibody effective in prevention and treatment of infectious diseases caused by P. aeruginosa and also a high titer human immunoglobulin preparation containing the monoclonal antibody. The inventors of the present invention have paid their special attention to a common structure in the O-antigens of different serotype strains of P. aeruginosa, and tried to establish a cell line producing a human monoclonal antibody specifically recognizing said common structure. As the result thereof, the inventors have succeeded in obtaining a human monoclonal antibody which specifically recognizes said common structure and binds to several serotype strains of P. aeruginosa. The human monoclonal antibody thus obtained is effective in prevention and treatment of P. aeruginosa infectious diseases. Specifically, the monoclonal antibody of the invention recognizes the common structure in the O-antigen of P. aeruginosa in serotypes A and H, thereby binding to almost all clinically isolated strains of P. aeruginosa belonging to these serotypes and exhibiting a strong prophylactic and therapeutic activity against the infectious diseases caused thereby. In the meantime, chemical structures of O-antigens of the standard strain IID1001 (serotype A) (J. Biochem., 104, 671–678 (1988)) and the standard strain IID1009 (serotype H) (J. Biochem., 105, 35–38 (1989)) are determined, and in these literatures, there are common structures mainly composed of N-acetyl-L-galactosaminuronic acid residue (cf. FIG. 1 of the accompanying drawing in which the upper structure belongs to the O-antigen of P. aeruginosa of Type A and the bottom structure belongs to that of Type H). It is therefore presumed that the monoclonal antibody according to the invention specifically recognizes this common structure mainly composed of N-acetyl-L-galactosaminuronic acid residue in the O-antigen of *P. aeriginosa* of serotypes A and H. Still, N-acetyl-L-galactosaminuronic acid residue is a very unique saccharide residue and has so far been found nowhere except in the O-antigen of serotypes A and H strains of *P. aeruginosa*. The conventionally prepared antisera against the O-antigen of the standard serotype strain does not show any binding property to this common structure. Further, there has been no report on the case where a certain mouse or human monoclonal antibody specifically recognizes such common structure in the O-antigen of the serotype A and H strains of *P. aeruginosa*. Thus, the inventors of the present application have established for the first time such a monoclonal antibody specifically recognizing said common structure.

An extensive investigation of binding mechanism of the monoclonal antibody and the structural analysis of antigen, particularly, the common structure of the O-antigen, has affirmed that the common structure to which the monoclonal antibody according to the invention shows a specific binding property is as mentioned above. In case of developing any prophylactic or therapeutic preparation based on a human monoclonal antibody, it is an important factor that the structure of the antigen to which said human monoclonal antibody binds has been identified. Thus, the monoclonal antibody according to the invention is extremely useful in this respect.

Accordingly, a primary object of the present invention is to provide a human monoclonal antibody which can specifically recognize the common structure of the O-antigen of *P. aeruginosa* of serotypes A and H and bind to strains of *P. aeruginosa* of serotypes A and H, and which is effective in prevention and treatment of infectious diseases caused by *P. aeruginosa* of said serotypes. Another object of the invention is to provide a high titer immunoglobulin preparations for prevention or treatment of infectious diseases caused by *P. aeruginosa*, which comprises at least one monoclonal antibody of the invention. A further object of the invention is to provide a human cell line being capable of producing said monoclonal antibody continuously. A still further object of the invention is to provide a processes for the production of said monoclonal antibody by culturing said human cell line. These and other objects of the present invention will be apparent to those skilled in the art from the foregoing and subsequent descriptions in the present specification. Still, "TS3G2" referred to in the subsequent working examples is the representative example of the monoclonal antibody of this invention.

The monoclonal antibody of the invention is intended to mean a human monoclonal antibody produced by a single antibody-producing clone, which antibody is capable of binding to strains of *P. aeruginosa* of serotypes A and H.

DETAILED DESCRIPTION OF THE INVENTION

Figure 1:
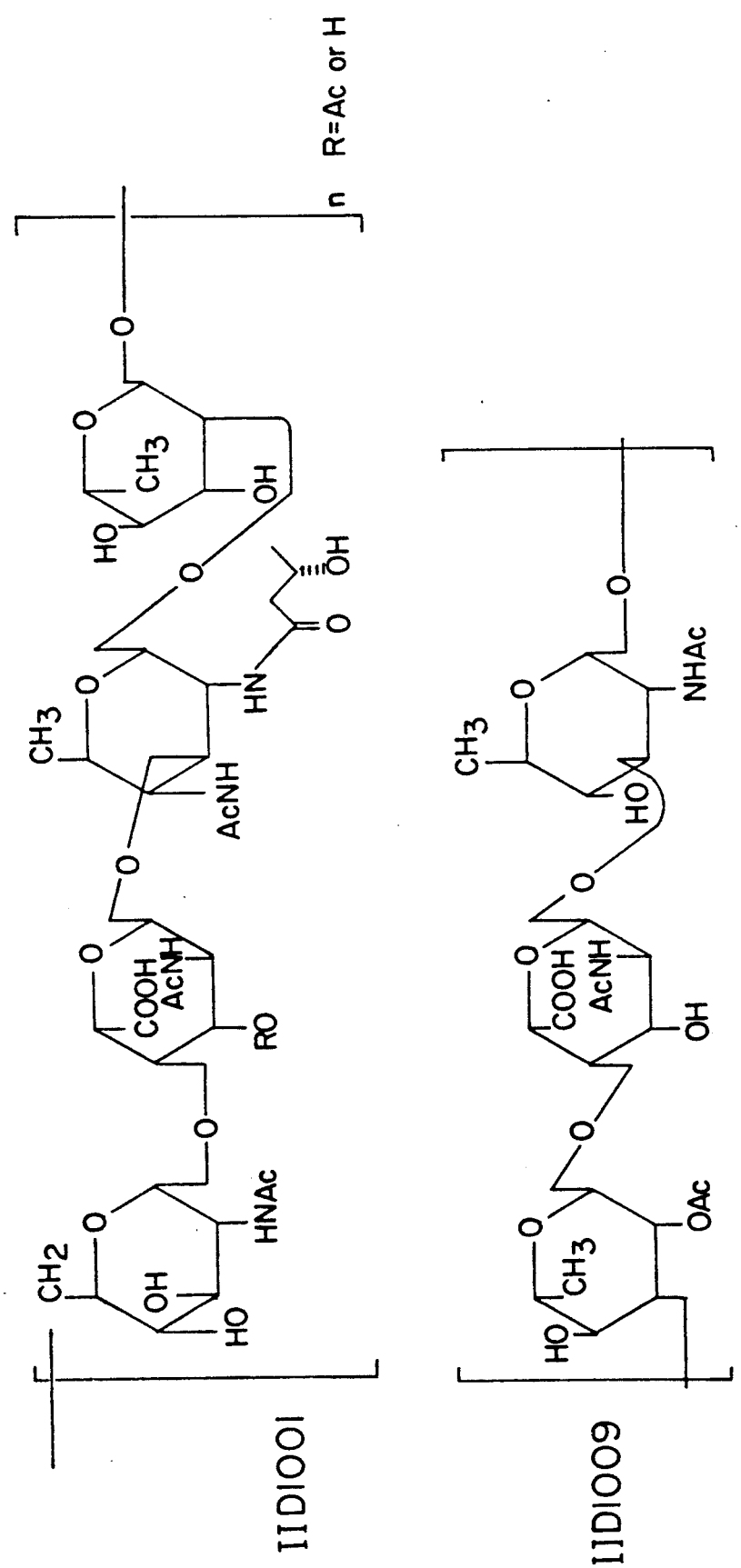
FIG. 1 shows the chemical structures of the O-antigens of *Pseudomonas aeruginosa* strains IID 1001 and IID 1009.

The monoclonal antibody of the invention can be prepared, for example, by the following procedures.

Human B lymphocytes sensitized with *P. aeruginosa* (living bacteria or killed bacteria with formalin or heating), or preferably LPS derived from *P. aeruginosa*, is subject to cell fusion with myeloma cell or B lymphobalstoid cell, and the resultant hybridoma is allowed to grow continuously in vitro, whereby a cell line capable of continuously producing the desired antibody is established. The established cell line is in vitro cultured, and the antibody secreted in the culture medium is extracted and purified to obtain the desired antibody in large quantities.

The serotype used herein is in accordance with the Classification pursuant to the Japanese Commitee, which is determined on the difference in immunological reaction using an antiserum or a mouse monoclonal antibody specifically reactive to the standard strain of *P. aeruginosa* of each serotype.

LPS stands for a lipopolysaccharide and constitutes a major component of an outer membrane of Gram-negative bacteria. LPS consists of (1) a glycolipid called lipid A, (2) an inner core oligosaccharide comprising 2-keto-3-deoxyoctonic acid, heptose, ethanolamine, phosphate, etc. as its constituents, (3) an outer core oligosaccharide of which constituents differ depending on species and which comprises, as far as *P. aeruginosa* is concerned, glucose, rhamnose, galactosamine, alanine, etc. as its constituents, and (4) a polysaccharide called O-antigen which determines the serotype.

The term "monoclonal antibody" herein used means an antibody having a uniform molecular structure and being produced by a single antibody-producing clone, which, in turn, can be obtained by a cell fusion (Nature, 256, 495 (1975)) or EB virus transformation (Proc. Natl. Acad. Scie., USA, 70, 190 (1973)).

Production of the human monoclonal antibody of the invention comprises the following steps: (1) preparation of human B lymphocytes sensitized with an antigen; (2) establishment of specific monoclonal antibody-producing cell lines by immortalizing the cells as prepared in (1); (3) cultivation of the cell lines as established in (2); (4) purification of the specific monoclonal antibody from the culture meduium as obtained in (3); and (5) production of an immunoglobulin preparation of high titer comprising the specific monoclonal antibody as purified in (4). Each of these steps will be hereinafter explained in detail.

Step (1):

As the human B lymphocytes, there may be used human B lymphocytes producing an antibody to the common structure in the O-antigen of *P. aeruginosa* of serotypes A and H and, which can be separated from a peripheral blood by the centrifugation using a lymphocyte separation liquid such as Lymphoprep ® or Mono-Poly Resolving Medium ® (Flow Lab.). There may be also used B lymphocytes originated from tissues or organs (e.g. lymphnode, spleen) extracted for the purpose of diagnosis or therapy of diseases, umbilical cord blood or the like. It is desirable to obtain the cells from persons who were infected with *P. aeruginosa* in the past and whose cells were sensitized with *P. aeruginosa*. Pertinent persons, from whom the cells may be obtained, can be chosen by previous measurement of the antibody titer in their sera against formalin-treated *P. aeruginosa* cell or LPS derived from *P. aeruginosa*. Alternatively, human B lymphocytes may be obtained from any person irrespective of his medical history in the past. Such lymphocytes are mixed with formalin-treated *P. aeruginosa*, or preferably LPS derived from *P. aeruginosa*, before use for cell fusion. Namely, *P. aeruginosa* killed by formalin-treatment or, preferably, LPS of

*P. aeruginosa* is added to B lymphocytes as an antigen. Further, solutions containing lymphokines such as B cell proliferation factors and B cell differentiation factors (e.g. plant lectins such as pokeweed mitogen (PWM), bacterial body components such as Cowan I, human lymphocyte mixed culture, spleen, thymus or umbilical cord blood cell culture) may be added to human B lymphocytes for sensitization in vitro, followed by proliferation and differentiation to give antibody-producing cells. The thus obtained human B lymphocytes can release a small amount of antibody for a certain limited period but they are not immortal.

Step (2):

For changing the above sensitized human B lymphocytes to continuously proliferable immortal cell lines, the sensitized human lymphocytes and myeloma cells are subjected to cell fusion in the presence of polyethylene glycol. The myeloma cells as used are hypoxanthine-guanine phosphoribosyl transferase (HGPRT)-deficient mutants (e.g. P3X63-Ag8(P3), P3X63-Ag8.653) originated from mouse myeloma cell, HGPRT-deficient mutant originated from human myeloma cell U-266, HGPRT-deficient mutants originated from mouse-human heteromyeloma cell which is obtained by cell fusion between mouse myeloma cell and human myeloma cell, or mouse myeloma cell and human B lymphocytes. HGPRT-deficient mutants originated from human B lymphoblastoid cell can be used in place of myeloma cell.

As the polyethylene glycol (PEG), there may be used, for instance, PEG 1,000 to 6,000 in a concentration of 30 to 50% (w/v). The fusion efficiency can be enhanced by incorporation of lectin, poly-L-lysine, dimethylsulfoxide, etc. thereto.

The fusion may be carried out, for instance, in the same manner as described in the Kohler et al. article (Nature, 256, 495 (1975)) wherein cell fusion is carried out to obtain a mouse-mouse hybridoma producing a mouse monoclonal antibody. For instance, the sensitized human B lymphocytes and HGPRT-deficient myeloma cells or human-mouse heteromyeloma cells are mixed together in a proportion of 3-1:1, and 45% (w/v) PEG 1500-6000 is added portionwise thereto in 0.5 to 1 minute, and the resultant mixture is allowed to stand for 0.5 to 3 minutes. To the resulting mixture, 10 to 50 ml of a culture medium containing no serum are added in 5 to 10 minutes, and subsequently 2 ml of FCS are added, and the mixture is incubated at 37° C. for 10 to 60 minutes. After centrifugation, fresh culture medium is further added thereto to make a cell concentration of $10^5$ to $10^6$/ml. The cell suspension thus obtained is inoculated into a 96 well microplate at a rate of $5\times10^4$ to $5\times10^5$ cells per well. On the next day, the half amount is replaced by a hypoxanthine-aminopterin-thymidine-containing medium (HAT medium) or a hypoxanthine-azaserine-containing medium (HAz medium), and cultivation is effected at 32 to 37° C. under 5% $CO_2$. For about 10 to 20 days, the culture medium is replaced by HAT medium or HAz medium, and subsequently by hypoxanthine-thymidine-containing medium (HT medium) or hypoxanthine-containing medium (H medium) for about 3 to 6 days. The replacement is done on half amount basis at intervals of 3 days for 2 or 3 weeks to obtain a proliferative colony, i.e. i.e. hybridoma. It is also possible to select a hybridoma by the combined use of metabolism inhibitors without using a HGPRT-deficient mutant.

The antibody titer of the culture medium against seventeen serotype standard strains of *P. aeruginosa* killed by formalin-treatment or against thier LPS is measured by enzyme linked immuno sorbent assay (ELISA) or radioimmunoassay (RIA), and the desired cell which produces the specific antibody reactive to several serotye strains of *P. aeruginosa* is selected with the aid of the Western blotting method. Cloning is repeated two or three times to obtain a stable cell line having a high proliferative property and a high specific antibody productivity.

The cell lines as established from sensitized human B lymphocytes according to the cell fusion (hybridoma) method can proliferate continuously and produce the specific antibody stably in a large amount.

Step (3):

The thus established hybridomas ($0.5-5\times10^5$ cells/ml) are cultured in a settled culture in a vessel such as a cell culture flask or plate by the use of a $CO_2$ incubator at 32° to 37° C. under 2 to 10% $CO_2$ or a spinner culture using a usual culture medium for animal cells. Particularly when culture is made at a large scale, a jar fermenter, a hollow fiber system or the like designed for animal cells may be used. The usual culture medium may be, for instance, a medium (RPMI1640, Eagle's MEM) containing 2 to 20% serum of bovine fetus, calf, cow, horse, human or the like, a serum-free medium containing supplements required for the growth of cells (e.g. insulin, transferrin, ethanolamine, selenite, bovine albumin, lipid or the like).

Cultivation of the hybridoma may also be conducted, in place of the in vitro cultivation mentioned above, by intraperitoneally inoculating and cultivating the hybridoma in animals such as a nude mouse. When a mouse or a nude mouse is employed, 0.5 to $2.5\times10^7$ cells per mouse is inoculated in peritoneal cavity. It is preferred to administer pristane or anti-asialo $GM_1$ antibody before inoculation. Radiation of X-ray or spleen extraction may also be helpful for successful inoculation.

Step (4):

Purification of the antibody may be carried out by conventional biochemical procedures (e.g. ammonium sulfate precipitation, ethanol precipitation, PEG fractionation, ion exchange chromatography, gel filtration, affinity chromatography, high performance liquid chromatography, electrophoresis). In the purification process, care should be taken for preventing the production of aggregation or the depression of antibody activity. For this purpose, human serum albumin (HSA) may be added in an amount of 0.05 to 2%. Addition of amino acids such as glycine or L-alanine, especially basic amino acids such as lysine, arginine or histidine, saccharides such as glucose or mannitol, salts such as sodium chloride, etc. may be sometimes preferred.

Step (5):

The purified monoclonal antibody may be formulated into a biological preparation by a per se conventional procedure comprising, for instance, filtering through a membrane filter for removal of bacteria, admitting into sterilized vials with stabilizers and freeze-drying.

The human monoclonal antibody preparation of the invention may comprise only one kind of human monoclonal antibody reactive to the common structure in the O-antigen of *P. aeruginosa* of two different serotypes for its use as a preventive or therapeutic agent for infections with *P. aeruginosa*. Preferably, the preparation comprises additionally at least one kind of human monoclonal antibody which can recognize the O-antigen of P. aerugionsa in any other serotypes. The preparation may also contain a human monoclonal antibody which can recognize any of other surface antigens of P. aeruginosa such as antigenic site other than O-antigen in LPS, outer membrane proteins, flagellum, and pilus, pathogenic factors of P. aeruginosa such as exotoxins, and exoenzymes (e.g. elastase and proteases), etc. The preparation of the invention may be employed after being combined with any conventional human immunoglobulin preparation. Further, the preparation may also be combined with any human monoclonal antibody to bacteria other than P. aeruginosa, virus, fungi, protozoa, cancer cells, and any conventional human immunoglobulin preparation. On the other hand, the human monoclonal antibody of the invention may be incorporated into a conventinal human immunoglobulin preparation to make a high titer immunoglobulin preparation to P. aeruginosa.

The human monoclonal antibody of the present invention binds to the surface of P. aeruginosa, particularly to the common structure in the O-antigen of P. aeruginosa of different serotypes. The binding of the antibody leads to the opsonization of the P. aeruginosa cell which enhances phagocytosis and killing and leads to the activation of complements which accelerates bacteriolysis. Accordingly, experimental mouse infections with P. aeruginosa can be treated by administration of the human monoclonal antibody of the invention.

For prevention and treatment of infectious diseases with P. aeruginosa or infections by bacterial containing P. aeruginosa, the human monoclonal antibody of the invention may be administered to an adult patient in an amount of about 0.5 to 500 mg, preferably 5 to 50 mg.

As stated above, a major advantageous merits of the human monoclonal antibody of the invention is that, since the antibody can recognize the common structure in the O-antigen of P. aeruginosa strains of serotypes A and H, it has a binding property to P. aeruginosa strains of serotypes A and H and shows an excellent therapeutic effect in the system of experimental mouse infections caused by the corresponding strains of P. aeruginosa. Other merits of the antibody of the invention are as follows.

Since it is a human-origin protein, any side effect (e.g. anaphylaxis) as seen on the administration of a heterogenic protein does not occur. Since it is produced from a certain specific cell line, a possibility of contamination with unknown biohazardous materials is much less in comparison with conventional immunoglobulins prepared from human blood originated from a number of unknown persons. The human monoclonal antibody of the invention is produced with a high antibody titer in vitro stably in a large amount, and its production process is more advantageous than conventional production processes using human blood in easy quality control.

The present invention will be hereinafter explained in detail by way of examples, to which it should not be limited in any way.

EXAMPLE 1

Establishment of human monoclonal antibody producing cell line TS3G2 by human-mouse cell fusion:

(1) Preparatin of human lymphocytes from peripheral blood and its cultivation

Peripheral blood (100 ml) having a high antibody titer against P. aeruginosa surface antigens was taken from a healthy volunteer (donor). To a centrifuge tube (50 ml, Sumitomo Bakelite) was added Mono-Poly Resolving Medium ® (15 ml) (Fow Lab.), and peripheral blood (20 ml) was slowly overlaid thereon, followed by centrifugation with a low speed centrifuge (BS-20BH, Tommy Precision Ind.) at 1,500 rpm and (Roter-TS-7) at room temperature for 30 minutes, whereby erythrocytes and lymphocytes were separated.

The portion containing lymphocytes was collected and washed three times with a Dulbecco's modified Eagle's minimum essential medium (hereinafter referred to as D-MEM), followed by calculation of the cell numbers to obtain lymphocyte cells of $1.1 \times 10^8$.

The lymphocyte cells ($1.1 \times 10^8$) were suspended in a lymphocyte-culturing medium (55 ml) containing formalin-killed cells of P. aeruginosa (IID1001 (Type A) and IID1002 (Type B), each 0.0002%), and the suspension was dispensed in 24 well microplates (Costar, #3424) at a rate of $2 \times 10^6$ lymphocyte cells/well and cultured at 37° C. under 5% $CO_2$ for 6 days. The lymphocyte-culturing medium just mentioned means RPMI-1640 medium which contains 20% (v/v) of inactivated fetal calf serum (FCS), 0.05 mg/ml of sodium pyruvate, $5 \times 10^{-5}$M of 2-mercaptoethanol, 30 µg/ml of transferrin derived from calf plasma (United States Biochemical Corp.) and 0.02% (v/v) of plant lectin derived from pokeweed (Gibco Lab.).

(2) Cell fusion

Human-mouse heteromyeloma cells (SHM-D33, ATCC No. CRL1668) were cultured in D-MEM containing 15% FCS, and $4 \times 10^7$ cells were washed twice with D-MEM.

On the other hand, peripheral blood lymphocytes cultured for 6 days in 24 well microplates according to Example 1(1) were recovered to give $8 \times 10^7$ lymphocyte cells. The cells were washed with D-MEM three times and mixed with the above human-mouse heteromyeloma cells in a centrifuge tube, followed by centrifugation to give precipitates.

To the precipitates in the centrifuge tube was added 1 ml of a polyethyleneglycol (PEG) solution (0.45 g of PEG4000 (Merck), 0.45 ml of PBS(-), and 0.1 ml of dimethylsulfoxide) in about one minute under rolling of the tube, and the mixture was left to stand at room temperature for one minute. D-MEM was then added to the tube at a rate of 2 ml/minute under rolling of the tube, which was repeated four times. By the use of D-MEM containing 10% FCS instead of D-MEM, the above procedure was repeated three times. Finally, 1.5 ml of FCS was added to the tube, and the mixture was left to stand for 20 minutes at 37° C. The cells were collected by centrifugation and suspended in 40 ml of D-MEM medium containing FCS (15%), sodium pyruvate (0.05 mg/ml), insulin (0.2 U/ml), oxaloacetic acid (0.15 mg/ml), azaserine (1 µg/ml), and hypoxanthine (100 µM), said medium being referred to as "HAz selective medium" hereinafter. The suspension was dispensed in 96 well microplates (Falcon #3040) at a rate of 100 µl per well so that one well might contain $1 \times 10^5$ myeloma cells. Each of the microplates had previously been charged with suspension of BALB/c mouse spleen cells and peritoneal exudate cells as feeder cells at a rate of 100 µl per well so that each well might contain BALB/c mouse spleen cells ($1 \times 10^5$) and BALB/c mouse peritoneal exudate cells ($1 \times 10^4$), and the plates had been incubated at 37° C. for one day under 5% $CO_2$. The microplates were incubated at 37° C. under 5% $CO_2$ and the half of the culture medium was replaced by HAz selection medium at 2 or 3 days interval. After one week, the half of the culture medium was replaced by H-medium which corresponds to azaserin-free HAz selective medium. After that, the half of the medium was replaced by azaserin and hypoxanthine-free hybridoma-culturing D-MEM medium, which is D-MEM medium containing FCS (15%), sodium pyruvate (0.05 mg/ml), insulin (0.2 U/ml), and oxaloacetic acid (0.15 mg/ml), at 2 or 3 days interval. Production of antibody to *P. aeruginosa* surface antigen was determined on culture supernatants of the wells which showed growth of the cells on the 26th day after the cell fusion, by ELISA using 96 well microplates (Falcon #3912) on which *P. aeruginosa* was fixed by glutaraldehyde. The standard strains of *P. aeruginosa* of seventeen different serotype according to Homma's classification were employed in the above test, which are obtainable from the Institute of Medical Science, Tokyo University, Japan, or from ATCC. The test revealed that one well produced IgG antibody which extensively reacted with standard strains of *P. aeruginosa* of serotypes A and H. The heterohybridoma in the well was further cultivated and cloned by means of the limitting dilution, whereby a cell line designated TS3G2, which stably produces human IgG antibody, was obtained. The term "TS3G2" may also be herein used as the name of the human monoclonal antibody produced by the cell line TS3G2. The hybridoma TS3G2 was deposited under the Budapest Treaty on Apr. 6, 1989 at the Fermentation Research Institute, Agency of Industrial Science and Technology, located at 1-3, Higashi 2-chome, Tsukuba-shi, Ibaraki-ken, Japan and assigned an accession number FERM BP-2372. The human monoclonal antibody TS3G2 was IgG ($\gamma_1$, K).

EXAMPLE 2

Study on binding spectrum of human monoclonal antibody TS3G2 by ELISA:

(1) Measurement of anti-*P. aeruginosa* antibody by ELISA

The antibody titer against *P. aeruginosa* surface antigen was measured as follows. *P. aeruginosa* was suspended in a phosphate buffered saline (pH 7.2; comprising NaCl (8 g/l), KCl (0.2 g/l), NaHPO$_4$.12H$_2$O (2.99 g/l and KH$_2$PO$_4$ (0.2 g/l ))) (PBS) to give absorbance of 0.2 at a wavelength of 600 nm. The suspension was charged in 96 well microplates (Falcon #3912) at a rate of 50 μl/well, followed by centrifugation at 2,000 rpm for 15 minutes. 2% Glutaraldehyde was added to each well at a rate of 50 μl/well to fix the bacterial cell to the microplates. After removal of the suspension from the microplates, 3% of bovine serum albumin (BSA) in PBS was charged to the microplate at a rate of 120 μl/well and incubated at 37° C. for 30 minutes for blocking of the unbound portion of the assay plate. The resulting microplate was used as the antigen-coated plate in the subsequent operation. When desired, storage of such microplate was made at −20° C.

Prior to the assay, the microplate was washed with a 0.05% Tween 20 containing PBS solution (PBST) three times.

PBST containing 1% BSA was charged into wells at a rate of 50 μl/well, and a sample (culture supernatant or purified IgG antibody), optionally diluted with PBST containing 1% BSA, was added thereto at a rate of 50 μl/well, followed by incubation at 37° C. for 2 hours. The sample was removed from the plate, which was washed with PBST three times. Alkaline phosphatase-labeled, affinity-purified anti-human immunoglobulin antibody (Kirkegaard & Perry Lab. Inc.) (secondary antibody) diluted with 1% BSA-containing PBS solution in 500 to 1,000 fold was added to the microplate at a rate of 100 μl/well for incubation at 37° C. for 2 hours. For measurement of the IgG antibody titer and the IgM antibody titer, there were respectively employed alkaline phosphatase-labeled anti-human IgG antibody and alkaline phosphatase-labeled anti-human IgM antibody.

After removal of the secondary antibody, the microplate was washed with PBST three times, and a substrate solution, i.e. an aqueous solution containing sodium p-nitrophenylphosphate (3 mg/ml) in 10% diethanolamine buffer (pH, 9.1) containing NaN$_3$ (0.2 mg/ml) and MgCl$_2$.6H$_2$O (0.1 mg/ml), was added to the microplate at a rate of 100 μl/well, followed by reaction at 37° C. The binding activity of the antibody (OD$_{405}$) was measured on Multiskan ® (Titertek).

(2) Binding property of TS3G2 to various serotype standard strains of *P. aeruginosa*.

The binding property of TS3G2 to various serotype standard strains of *P. aeruginosa* was examined by ELISA as described in Example 2(1). The strains were obtained from the Institute of Medical Science, Tokyo University, Japan, and cultivated in heart infusion agar medium. The test results are shown in Table 2.

TABLE 2

Binding activity of TS3G2 to various serotype standard strains of *P. aeruginosa* according to The Japnese Commttee' Classification

| Serotype | Strain | ELISA Value (OD$_{405}$) |
|---|---|---|
| A | IID 1001 (ATCC27577) | 0.67 |
| B | IID 1002 (ATCC27578) | 0.03 |
| B | IID 1007 (ATCC27583) | 0.04 |
| B | IID 1013 (ATCC27589) | 0.04 |
| B | IID 5004 | 0.03 |
| C | IID 1021 | 0.02 |
| D | IID 1004 (ATCC27580) | 0.03 |
| E | IID 1130 | 0.04 |
| F | IID 1006 (ATCC27582) | 0.04 |
| G | IID 1008 (ATCC27584) | 0.03 |
| H | IID 1009 (ATCC27585) | 1.52 |
| I | IID 1010 (ATCC27586) | 0.03 |
| J | IID 1011 (ATCC27587) | 0.04 |
| K | IID 1012 (ATCC27588) | 0.03 |
| L | IID 5141 | 0.05 |
| M | IID 5018 | 0.01 |
| M | IID 1015 | 0.03 |

The table shows that TS3G2 was bound selectively to the serotype standard strains of Types A and H of *P. aeruginosa*.

(3) Binding property of TS3G2 to clinical isolates

It was shown in the above test that TS3G2 could bind to the serotype standard strains of Types A and H. Consequently, binding property of TS3G2 to several clinical isolates classified to Type A (19 strains) and Type H (12 strains) was examined. As shown in Table 3 below, TS3G2 bound to all these strains. For comparison, Types B, E, G, I and M clinical isolates (about 20 strains of each serotypes), which are isolated from patients with high frequency, were subjected to the same test but any of these isolates did not bind to TS3G2.

TABLE 3

| Binding activity of TS3G2 to clinical isolates | | |
|---|---|---|
| Serotype | Strain | ELISA Value (OD$_{405}$) |
| A | SP6745 | 1.99 |
|   | SP6746 | 2.23 |
|   | SP6783 | 2.34 |
|   | SP6818 | 2.39 |

TABLE 3-continued

Binding activity of TS3G2 to clinical isolates

| Serotype | Strain | ELISA Value (OD$_{405}$) |
|---|---|---|
|  | SP6830 | 2.29 |
|  | SP6840 | 2.39 |
|  | SP6708a | 1.93 |
|  | SP9710 | 2.36 |
|  | SP9711 | 2.33 |
|  | SP9731 | 2.29 |
|  | SP9762 | 2.29 |
|  | SP9763 | 2.37 |
|  | SP9768 | 2.39 |
|  | SP9780 | 2.40 |
|  | SP10029 | 2.26 |
|  | SP10040 | 2.37 |
|  | SP10060 | 2.38 |
|  | SP10648 | 2.38 |
|  | SP10678 | 2.37 |
| H | SP6931 | 2.41 |
|  | SP7503 | 2.53 |
|  | SP7507 | 2.45 |
|  | SP7514 | 2.41 |
|  | SP7520 | 2.39 |
|  | SP7522 | 2.37 |
|  | SP7532 | 2.35 |
|  | SP7525 | 2.53 |
|  | SP10054 | 1.67 |
|  | SP10068 | 1.83 |
|  | SP10678 | 2.38 |
|  | SP10681 | 1.86 |
| Negative control | (−) | 0.02 |

EXAMPLE 3

Characterization of the antigen recognized by the human monoclonal antibody TS3G2 with competitive ELISA:

(1) Preparation of lipopolysaccharide (LPS)

LPS were collected from serotype standard strains of P. aeruginosa, i.e. IId1001 (Type A) and IID1009 (Type H), according to the method described by Westphal and Jonn (Methods Carbohydr., Chem., 5, 83–91 (1965)). Thus, the P. aeruginosa strain was cultured to the late exponential phase in heart-infusion broth medium (Nissui Pharmaceuticals), and the cells were collected by centrifugation. The wet cells were treated with 45% phenol at 68° C. and centrifuged at 3,000 rpm for 15 minutes at a temperature of 10° C., whereby LPS was extracted in an aqueous layer. The aqueous layer was treated with cetyltrimethylammonium bromide to remove nucleic acids and precipitated with ethanol to give the standard LPS.

(2) Study on the antigen recognized by TS3G2 with competitive ELISA

Using preparations of LPS derived from IID1001 or IID1009 of P. aeruginosa as prepared in (1) above as the competitive substances, the antigen recognized by TS3G2 was examined by ELISA. Namely, a mixture of the competitor and the antibody was incubated at 37° C. for 1 hour and subjected to ELISA using 96 well microplates on which standard strain IID1009 of P. aeruginosa cells had been coated, whereby the rate of inhibition was measured. The results are shown in Table 4.

TABLE 4

Study of the antigen recognized by TS3G2 with competitive ELISA

| Competitive substance | Concentration (μg/ml) | Rate of inhibition (%) |
|---|---|---|
| IID1001 LPS | 0 | 0 |
| " | 0.05 | 52 |
| " | 0.5 | 88 |
| " | 5 | 96 |
| " | 50 | 98 |
| IID1009 LPS | 0 | 0 |
| " | 0.05 | 0 |
| " | 0.5 | 54 |
| " | 5 | 84 |
| " | 50 | 96 |

The above test results show that the binding of TS3G2 to the standard strain IID1009 is inhibited by both of LPS derived from IID1001 and IID1009 in dose dependently. This means that the antigenic determinant recognized by TS3G2 resides in LPS of IID1001 and IID1009.

EXAMPLE 4

Characterization of the antigen recognized by human monoclonal antibody TS3G2 by Western blotting analysis:

LPS derived from IID1001 and IID1009 as obtained in Example 3(1) was treated with a sample buffer comprising Tris buffer (31 mM), pH 6.8, SDS (1.5%), glycerol (5%), mercaptoethanol (2.5%), and Bromphenol blue (0.005%) at 100° C. for 5 minutes, subjected to electrophoresis on 12.5% polyacrylamide gel containing 0.2% SDS, and transferred to Durapore ® filter (Millipore). On the membrane, the antigen recognized by human monoclonal antibody TS3G2 was identified by immuno staining method employing alkaline phosphatase-conjugated goat anti-human IgM antibody (Kirkegaard & Gaithersburg Perry Lab. Inc.). As detecting phoretic pattern of LPS, the same test sample was electrophorated in the same manner, and the gel was developed by silver staining using Bio Rad kit.

The silver staining showed in higher molecular weight region the presence of a group of bands in ladder shape due to smooth type LPS which contains O-polysaccharide. The characteristic electrophoretic pattern of LPS are attributable to heterogeneity of the numbers of the repeating unit of the O-polysaccharide. Single broad band or a few bands observed in lower molecular weight region is assigned to LPS of R type or SR type, which lacks O-polysaccharide or has only a few repeating units.

As the results, strong binding was observed in both LPS derived from IID1001 and IID1009 in higher molecular weight region, i.e. in the region corresponding to the bands in ladder shape which comprise smooth type LPS having O-polysaccharide repeating structure. Binding was also observed in LPS of SR type having a few repeating units of O-polysaccharide but not in LPS of R type having no O-polysaccharide.

This study clearly suggests that the human monoclonal antibody TS3G2 recognizes specifically the O-antigen (O-polysaccharide) in the IID1001 and IID1009 derived LPS.

EXAMPLE 5

Separation and fractionation of polysaccharide moiety of lipopolysaccharide of P. aeruginosa and study on binding properties of resultant fractions to human monoclonal antibody TS3G2:

(1) Separation of polysaccharide portion of LPS of *P. aeruginosa* IID1001 and IID1009

According to Wilkinson & Gilbraith's method (Eur. J. Biochem., 52, 331 (1975)), polysaccharide portion was separated from LPS of *P. aeruginosa* IID1001 and IID1009 and the polysaccharide obtained was fractionated. Namely, LPS (10 mg) was dissolved in 10 ml of 1% acetic acid and heated at 100° C. for 90 minutes to selectively hydrolyze the ketosidic linkage in 2-keto-3-deoxyoctonate (KDO) residue present in the inner core of LPS. The reaction mixture was extracted with chloroform to obtain lipid A preparation from a chloroform layer. For fractionation, an aqueous layer from which free lipid A had thus been removed was subjected to Sephadex® G-50 column chromatography (Pharmacia, Uppsala) (column size: 1×70 cm) equilibrated with 50 mM pyridine/acetate buffer, pH 5.5. Elution of polysaccharide, SR core oligosaccharide, and R core oligosaccharide was detected by the colorimetric determination described hereinafter.

Neutral sugars were detected by the phenolsulfuric acid method (M. Dubois. et al., Anal. Chem. 28, 350 (1956)). Amino sugars were detected by hydrolyzing the sample with 2N $H_2SO_4$ at 100° C. for 2 hours and subjecting the hydrolyzed product to MBTH (3-methyl-2-benzothiazolinone hydrazone hydrochloride) method (A. Tsuji et al., Chem. Pharm. Bull., 17 217 (1969)).

Polysaccharide fractions containing repeating units of O-polysaccharides were obtained. Separation between the fraction of SR core oligosaccharide containing a few repeating units of O-polysaccharide and the fraction of R core oligosaccharide lacking O-polysaccharide was not sufficient, so that these types were combined to make a SR and R mixed core oligosacbharide fractions. Each fraction was freeze-dried for recovery.

(2) Binding property of human monoclonal antibody TS3G2 to each fraction derived from lipopolysaccharide Competitive ELISA was used for studying the binding property of TS3G2 to respective fractions containing the polysaccharide, the R and SR mixed core oligosaccharide, and the lipid A originated from *P. aeruginosa* IID1001 and IID1009 as obtained in (1) above. Thus, a mixture of the competitor and the antibody was incubated at 37° C. for one hour and subjected to ELISA using 96 well microplates on which *P. aeruginosa* standard strains IID1001 and IID1009 had been coated, whereby the rate of inhibition was measured. The results are shown in Table 5.

TABLE 5

Binding property of TS3G2 to fractions of polysaccharide and core oligosaccharide of SR and R mixed type

| Cell plate | Competitive substance | Concentration (µg/ml) | Rate of inhibition (%) |
|---|---|---|---|
| IID1001 Coated plate | IID1001 Polysaccharide fraction | 0 | 0 |
| | | 0.005 | 8 |
| | | 0.05 | 12 |
| | | 0.5 | 44 |
| | | 5 | 98 |
| | | 50 | 100 |
| IID1001 Coated plate | IID1001 SR + R type Core oligosaccharide fraction | 0 | 0 |
| | | 0.005 | 0 |
| | | 0.05 | 6 |
| | | 0.5 | 8 |
| | | 5 | 14 |
| | | 50 | 56 |

TABLE 5-continued

Binding property of TS3G2 to fractions of polysaccharide and core oligosaccharide of SR and R mixed type

| Cell plate | Competitive substance | Concentration (µg/ml) | Rate of inhibition (%) |
|---|---|---|---|
| IID1009 Coated plate | IID1009 Polysaccharide fraction | 0 | 0 |
| | | 0.005 | 0 |
| | | 0.05 | 0 |
| | | 0.5 | 18 |
| | | 5 | 54 |
| | | 50 | 90 |
| IID1009 Coated plate | IID1009 SR + R type Core oligosaccharide fraction | 0 | 0 |
| | | 0.005 | 0 |
| | | 0.05 | 0 |
| | | 0.5 | 2 |
| | | 5 | 2 |
| | | 50 | 4 |

In either case of strains IID1001 and IID1009, the binding property of TS3G2 to the *P. aeruginosa* coated plate was largely inhibited by the presence of the polysaccharide fractions, whereas, in case of the SR and R mixed type core oligosaccharide, it was inhibited only with a high concentration of fractions. It follows therefrom that the inhibiting activity is attributable to the O-polysaccharide structure.

When the lipid A preparation was used as the competitive substance, no inhibition was observed even at such a high concentration as 50 µg/ml. It is therefore presumed that TS3G2 has no binding property to lipid A.

Based on the above results, it is concluded that the human monoclonal antibody TS3G2 specifically recognized the O-antigen (O-polysaccharide) in LPS derived from IID1001 and IID1009. Namely, the human monoclonal antibody TS3G2 is speculated to specifically recognize the common structure mainly composed of N-acetyl-L-galactosaminuronic acid residue being determined in the standard strains of *P. aeruginosa* of these serotypes.

EXAMPLE 6

Therapeutic effect of human monoclonal antibody TS3G2 on experimental *P. aeruginosa* infections in mice:

Therapeutic effect of human monoclonal antibody TS3G2 on mice experimental infections caused by clinical isolates of *P. aeruginosa*, each two strains of serotypes A and H, was examined. ICR strain mice (4 week old; male; 10 animals per group) were intraperitoneally challenged with a suspension containing the *P. aeruginosa* strain and 5% mutin. After one hour, the antibody TS3G2 (0.4 or 0.6 µg/head) was administered intraperitoneally. Judgement of the therapeutic effect was made based on the survival rate after one week. The test results are shown in Tables 6 and 7, from which it is understood that the antibody TS3G2 is effective in treatment of the experimental infections caused by several strains of *P. aeruginosa* of serotypes A and H.

TABLE 6

Therapeutic effect of TS3G2 on mice infected with clinical isolates of *P. aeruginosa* of serotype A

| Strain | Dose (µg/head) | Survival Rate (%) (Inoculated Amount: CFU/head) | | | |
|---|---|---|---|---|---|
| | | $4.8 \times 10^4$ | $0.9 \times 10^5$ | $9.5 \times 10^5$ | $4.8 \times 10^6$ |
| SP6783 | 0.4 | 100 | 100 | 100 | 10 |
| " | — | 80 | 20 | 10 | 0 |
| SP6818 | 0.4 | 100 | 100 | 90 | 0 |

TABLE 6-continued

Therapeutic effect of TS3G2 on mice infected with clinical isolates of *P. aeruginosa* of serotype A

| | | Survival Rate (%) | | | |
|---|---|---|---|---|---|
| | Dose | (Inoculated Amount: CFU/head) | | | |
| Strain | (μg/head) | 4.8 × 10⁴ | 0.9 × 10⁵ | 9.5 × 10⁵ | 4.8 × 10⁶ |
| " | — | 100 | 10 | 0 | 0 |

TABLE 7

Therapeutic effect of TS3G2 on mice infected with clinical isolates of *P. aeruginosa* of serotype H

| | | Survival Rate (%) | | |
|---|---|---|---|---|
| | Dose | (Inoculated Amount: CFU/head) | | |
| Strain | (μg/head) | 3.5 × 10⁵ | 1.8 × 10⁶ | 7 × 10⁶ |
| SP6896 | 0.6 | 100 | 80 | 50 |
| " | — | 50 | 10 | 40 |
| SP7532 | 0.6 | 100 | 80 | 30 |
| " | — | 80 | 30 | 10 |

What is claimed is:

1. A human monoclonal antibody, which is produced from hybridoma TS3G2, having the Accession No. FERM BP-2372.

2. Hybridoma TS3G2 (FERM BP-2372) or a descendant cell line originated therefrom.

3. A process for producing a human monoclonal antibody, which comprises culturing the hybridoma of claim 2, and recovering the produced antibody from the resultant culture.

* * * * *